(12) United States Patent
Chavez et al.

(10) Patent No.: US 10,368,994 B2
(45) Date of Patent: *Aug. 6, 2019

(54) RECESSED BURR HOLE COVERS AND METHODS FOR USING THE SAME

(71) Applicant: NeuroPace, Inc., Mountain View, CA (US)

(72) Inventors: Alfonso Chavez, San Jose, CA (US); Peter B. Weber, San Francisco, CA (US)

(73) Assignee: NeuroPace, Inc., Mountain View, CA (US)

(*) Notice: Subject to any disclaimer, the term of this patent is extended or adjusted under 35 U.S.C. 154(b) by 118 days.

This patent is subject to a terminal disclaimer.

(21) Appl. No.: 15/402,047

(22) Filed: Jan. 9, 2017

(65) Prior Publication Data

US 2017/0119527 A1     May 4, 2017

Related U.S. Application Data

(63) Continuation of application No. 13/792,165, filed on Mar. 10, 2013, now Pat. No. 9,572,973.

(51) Int. Cl.
*A61F 2/28*     (2006.01)
*A61N 1/05*     (2006.01)

(52) U.S. Cl.
CPC .......... *A61F 2/2875* (2013.01); *A61N 1/0539* (2013.01); *A61N 1/0534* (2013.01)

(58) Field of Classification Search
CPC ............ A61B 17/3403; A61B 17/3415; A61B 17/3417; A61B 17/3421; A61B 17/3423; A61B 17/3462; A61B 2017/3405; A61B 2017/3411; A61B 2017/3419; A61B 2017/3464; A61B 2017/3466; A61B 2017/347; A61B 90/10; A61B 90/11; A61B 90/14; A61B 2090/103; A61B 19/201;

(Continued)

(56) References Cited

U.S. PATENT DOCUMENTS

| | | | |
|---|---|---|---|
| 4,328,813 | A | 5/1982 | Ray |
| 5,464,446 | A | 11/1995 | Dreesen et al. |

(Continued)

FOREIGN PATENT DOCUMENTS

| | | |
|---|---|---|
| WO | 2001076498 | 10/2001 |
| WO | 2004103468 | 12/2004 |

*Primary Examiner* — Eric J Rosen
*Assistant Examiner* — Chima U Igboko
(74) *Attorney, Agent, or Firm* — Loza & Loza, LLP; David S. Sarisky

(57) ABSTRACT

A burr hole cover is configured to be recessed in a burr hole formed in a patient and includes a base and a cap provided with complementary features to allow a portion of a medical device, such as a brain lead, to be situated in the burr hole cover and then secured by rotation of the cap relative to the base. The features include channels on the base and matching cut-outs on the cap, and slots and locking pockets on the base that are configured to be aligned with locking tabs and locking protrusions on the cap. Because the burr hole cover is recessed in the burr hole, the medical device can extend proximally of the burr hole at the level of the cranium. A bottom surface of the cap may be provided with guides for the lead extending distally in towards the brain.

10 Claims, 18 Drawing Sheets

(58) Field of Classification Search
CPC .. A61M 2039/0261; A61M 2039/0223; A61M 2039/0288; A61M 39/0247; A61M 39/0208; A61N 1/0539; A61N 1/0558; A61N 1/0534; A61F 2/2875
USPC .................................................. 600/393, 394
See application file for complete search history.

(56) References Cited

U.S. PATENT DOCUMENTS

| | | |
|---|---|---|
| 5,843,150 A | 12/1998 | Dressen et al. |
| 5,865,842 A | 2/1999 | Knuth et al. |
| 5,865,843 A | 2/1999 | Baudino et al. |
| 5,927,277 A | 7/1999 | Baudino et al. |
| 6,044,304 A | 3/2000 | Baudino |
| 6,134,477 A | 10/2000 | Knuteson et al. |
| 6,210,417 B1 | 4/2001 | Baudino et al. |
| 6,319,241 B1 | 11/2001 | King et al. |
| 6,321,104 B1 | 11/2001 | Gielen et al. |
| 6,356,792 B1 * | 3/2002 | Errico .................. A61N 1/0534 606/129 |
| 6,795,737 B2 | 9/2004 | King et al. |
| 6,810,285 B2 | 10/2004 | Pless et al. |
| 6,902,569 B2 | 6/2005 | Parmer et al. |
| 7,204,840 B2 | 4/2007 | Skakoon et al. |
| 7,235,084 B2 | 6/2007 | Skakoon et al. |
| 7,580,756 B2 | 8/2009 | Schulte et al. |
| 7,604,644 B2 | 10/2009 | Schulte et al. |
| 7,636,596 B2 | 12/2009 | Solar |
| 7,637,915 B2 | 12/2009 | Parmer et al. |
| 7,660,621 B2 | 2/2010 | Skakoon et al. |
| 7,704,260 B2 | 4/2010 | Skakoon et al. |
| 7,744,606 B2 | 6/2010 | Miller et al. |
| 7,766,394 B2 | 8/2010 | Sage et al. |
| 7,815,651 B2 | 10/2010 | Skakoon et al. |
| 7,828,809 B2 | 11/2010 | Skakoon et al. |
| 7,833,231 B2 | 11/2010 | Skakoon et al. |
| 7,857,820 B2 | 12/2010 | Skakoon et al. |
| 7,949,410 B2 | 5/2011 | Rodriguez |
| 7,976,530 B2 | 7/2011 | Johnson et al. |
| 7,988,674 B2 | 8/2011 | Adams et al. |
| 8,116,850 B2 | 2/2012 | Solar |
| 8,152,792 B1 | 4/2012 | Kornel |
| 8,192,445 B2 | 6/2012 | Parmer et al. |
| 8,845,656 B2 | 9/2014 | Skakoon et al. |
| 8,911,452 B2 | 12/2014 | Skakoon et al. |
| 2005/0182421 A1 | 8/2005 | Schulte et al. |
| 2005/0182422 A1 | 8/2005 | Schulte et al. |
| 2005/0182424 A1 | 8/2005 | Schulte et al. |
| 2005/0182425 A1 | 8/2005 | Schulte et al. |
| 2009/0112327 A1 * | 4/2009 | Lane .................... A61N 1/0539 623/17.19 |
| 2009/0306750 A1 | 12/2009 | Boling et al. |
| 2009/0326610 A1 | 12/2009 | Pless et al. |
| 2010/0179563 A1 | 7/2010 | Skakoon et al. |
| 2010/0312193 A1 | 12/2010 | Stratton |
| 2011/0270187 A1 | 11/2011 | Nelson |
| 2013/0066410 A1 * | 3/2013 | Funderburk .......... A61F 2/2875 607/116 |

* cited by examiner

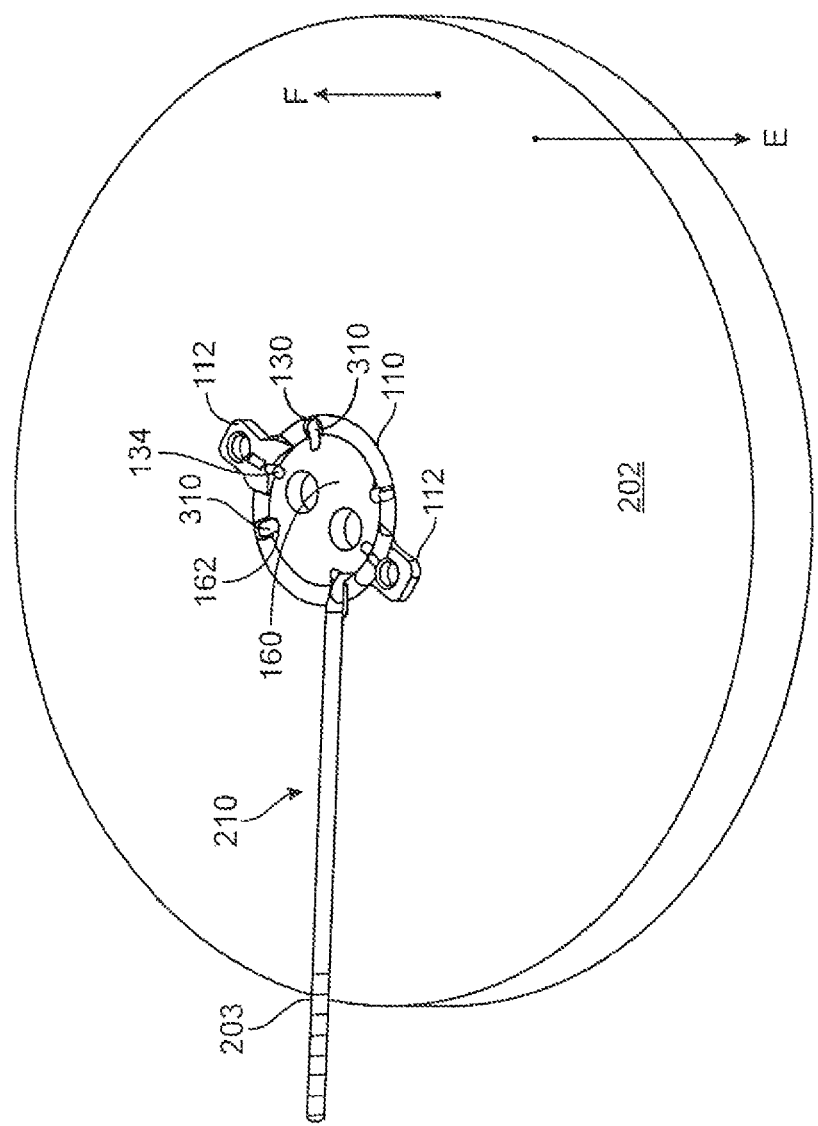

SEE DETAIL A    SECTION A-A

DETAIL A

RECESSED BURR HOLE COVERS AND METHODS FOR USING THE SAME

CROSS-REFERENCE TO RELATED APPLICATION(S)

This application is a continuation of U.S. application Ser. No. 13/792,165, entitled "Recessed Burr Hole Covers and Methods for Using the Same," filed on Mar. 10, 2013, now U.S. Pat. No. 9,572,973, which is expressly incorporated by reference herein in its entirety.

BACKGROUND

Field

The present technology relates generally to apparatuses and methods for securing a medical instrument, such as a lead, within a burr hole.

Background

Increasingly, leads associated with electrodes or other components that can be used for sensing signals from or delivering a form of modulation to a patient's neural tissue are partially implanted in a patient's brain through a burr hole that is formed (e.g., using a drill fitted with a special drill bit) in the patient's cranium (cranial bone or skull). To prepare for forming the burr hole, the scalp over the site is removed or temporarily retracted. After the burr hole is formed, a portion of a lead is implanted through the burr hole so that electrodes or other components that are associated with the lead are distally located at a desired target or targets in the brain. Once a distal portion of a lead is positioned at the target(s), it may be desirable to secure a proximal portion of the lead in the vicinity of the burr hole in the hopes of minimizing the extent to which the distal portion of the lead will shift, for example, away from the target(s), for so long as the lead is intended to remain implanted in the patient and to function for its intended purpose(s).

BRIEF DESCRIPTION OF THE DRAWINGS

FIG. 3 is a perspective view illustrating a portion of a lead extending proximally of a burr hole cover, according to an embodiment, after the burr hole cover is installed in a burr hole, in a schematic representation of a portion of a patient's cranium.

Figure 1A:
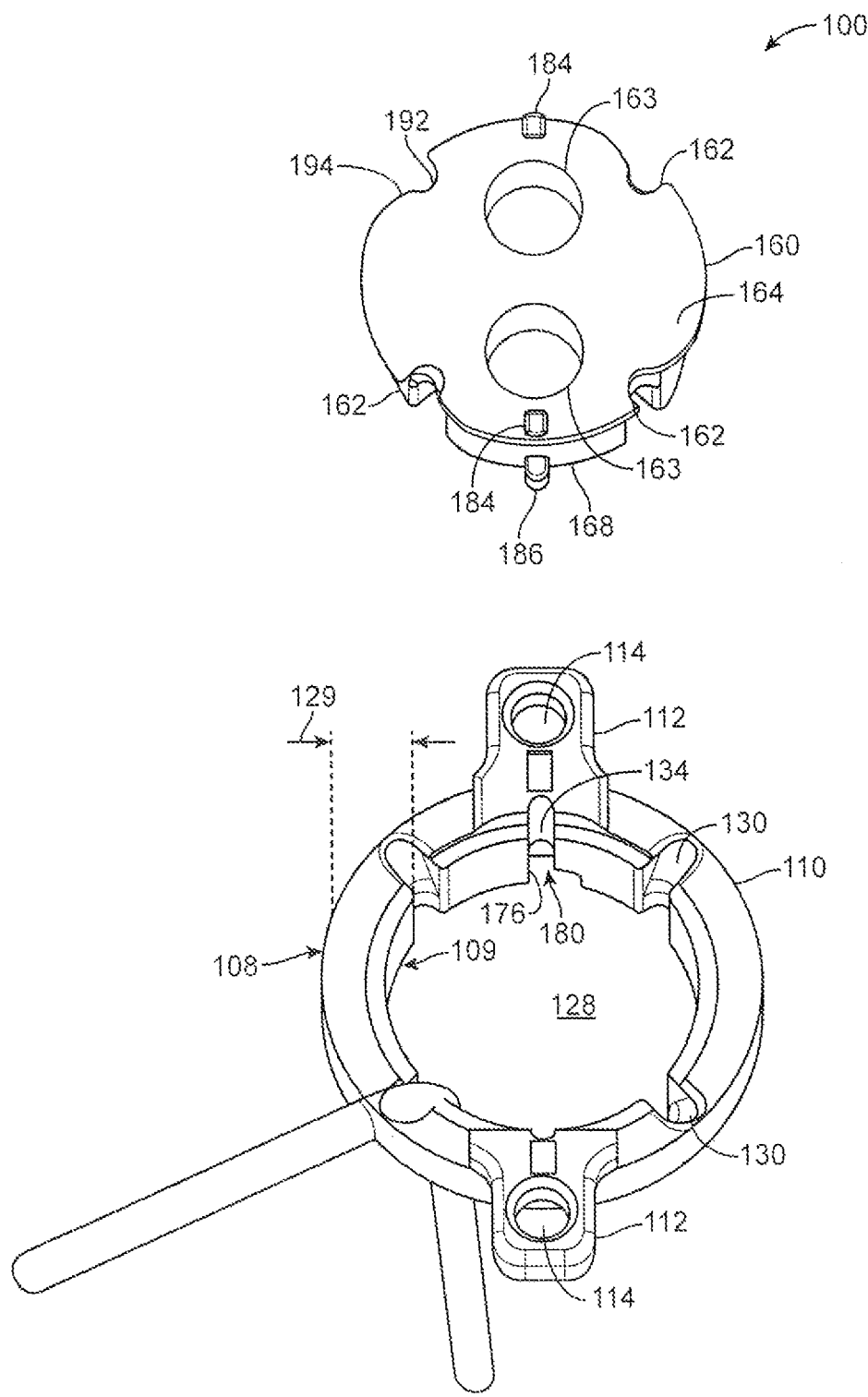
FIG. 1A is an exploded perspective view of a burr hole cover and a portion of a medical lead according to an embodiment.

The drawings referred to in this description should not be understood as being drawn to scale unless specifically noted.

DETAILED DESCRIPTION

Various embodiments are described below, with reference to detailed illustrative embodiments, in the context of burr hole covers. It will be apparent that the apparatuses and methods described herein can be embodied in a wide variety of forms. Consequently, the specific structural and functional details disclosed herein are representative and do not limit the scope of embodiments.

Embodiments of a burr hole cover are provided for securing a segment of a medical device relative to a burr hole formed in the cranium of a patient when a distal portion of the medical device is implanted or otherwise introduced into the burr hole interiorly of the patient. The embodiments are described primarily with reference to the medical device being an electrode-bearing lead, such as might be used in an application for deep brain stimulation or direct brain stimulation such as responsive stimulation such as those applications under investigation by NeuroPace, Inc. of Mountain View, Calif. It should be appreciated, however, that the burr hole cover may be used with good results to secure a segment of a different type of medical device, such as a catheter with an appropriate diameter or other medical instrument, relative to a burr hole prior to and/or during use of the medical device in its intended application. Similarly, it should be appreciated that, in some circumstances, embodiments of a burr hole cover described herein may be used to secure more than one medical device simultaneously (e.g., two leads) for some applications.

Generally, when a medical device is introduced to a target position interiorly of a patient's cranium, it is desirable for the distal portion of the medical device not to move appreciably from that target. More particularly, in the case where the medical device is a deep brain lead with one or more electrodes associated with a distal portion thereof, it is desirable to minimize the degree to which the distal portion moves once it has been positioned at the target. For example, in an application in which one or more of the electrodes are intended to be used in stimulation pathways to deliver a form of electrical stimulation therapy to the tissue surrounding or adjacent the electrodes, and the electrodes on the distal portion of the lead are positioned at a desired target area of the patient's brain (for example, the subthalamic nucleus (STN) or a brain location suspected or known to be a focus or related to a focus of an epileptic seizure), it would be desirable to avoid moving the electrodes from that target area during the time over which it is anticipated the therapy may be delivered. Similarly, in an application in which electrodes or other elements associated with the distal portion of a lead are going to be used to sense physiological activity from a location in the brain, it would be desirable to avoid dislodging the sensors from the desired sensing location once the lead is implanted for so long as sensing potentially may occur.

Applications are known or under investigation in which leads for delivering stimulation therapy (and/or sensing and/or recording the electrical activity of nerve cells) are implanted and then left in place for extended period of time (e.g., on the order of years provided the leads remain intact and uncompromised and otherwise without complications). Desirably, then, the means and methods by which the lead is discouraged from moving away from the target area will be relatively robust and durable and therefore well-suited for chronic or long-lasting applications involving the lead or other medical device. It may be desirable to form a burr hole cover from a material or materials that will not interfere with any imaging procedure to which the patient might be subjected (e.g., materials that will not distort or obstruct an image) and/or from material(s) (e.g., non-magnetic materials) that will not contraindicate an imaging procedure in the first instance. In addition, the material(s) from which the burr hole cover is formed desirably will not degrade appreciably over time and will be biocompatible with any body surfaces (e.g., cranial bone) and body fluids (e.g., cerebral spinal fluid) with which the burr hole cover may come in contact throughout the time the burr hole cover is installed in the patient.

Referring to FIGS. 1-15, embodiments of burr hole covers and embodiments of methods of using burr hole covers will be described.

FIG. 1A is an exploded view of an embodiment of a two-component burr hole cover 100. The two components are a base 110 and a cap 160. Each component of the burr hole cover 100 is described in more detail below.

Figure 2A:
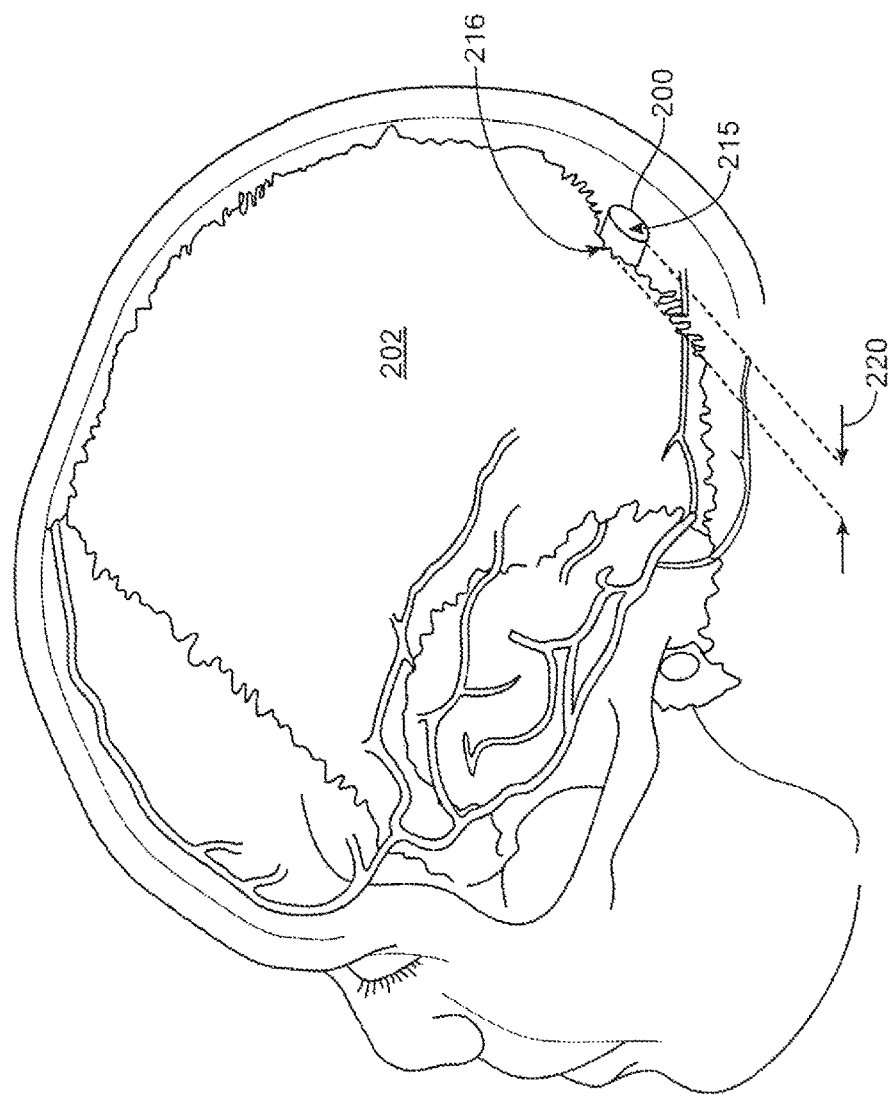
FIG. 2A is a schematic view of a patient's skull with a burr hole formed therein.

Referring now to FIG. 2A, a burr hole 200 is formed (for example, using a drill) in a cranial bone or cranium 202 of a patient. The burr hole 200 extends from a burr hole top 215 at an outer surface of the cranium to a burr hole bottom 216 at an inner surface of the cranium (towards the brain). A burr hole depth 220 can be measured between the burr hole top 215 and bottom 216.

Figure 2B:
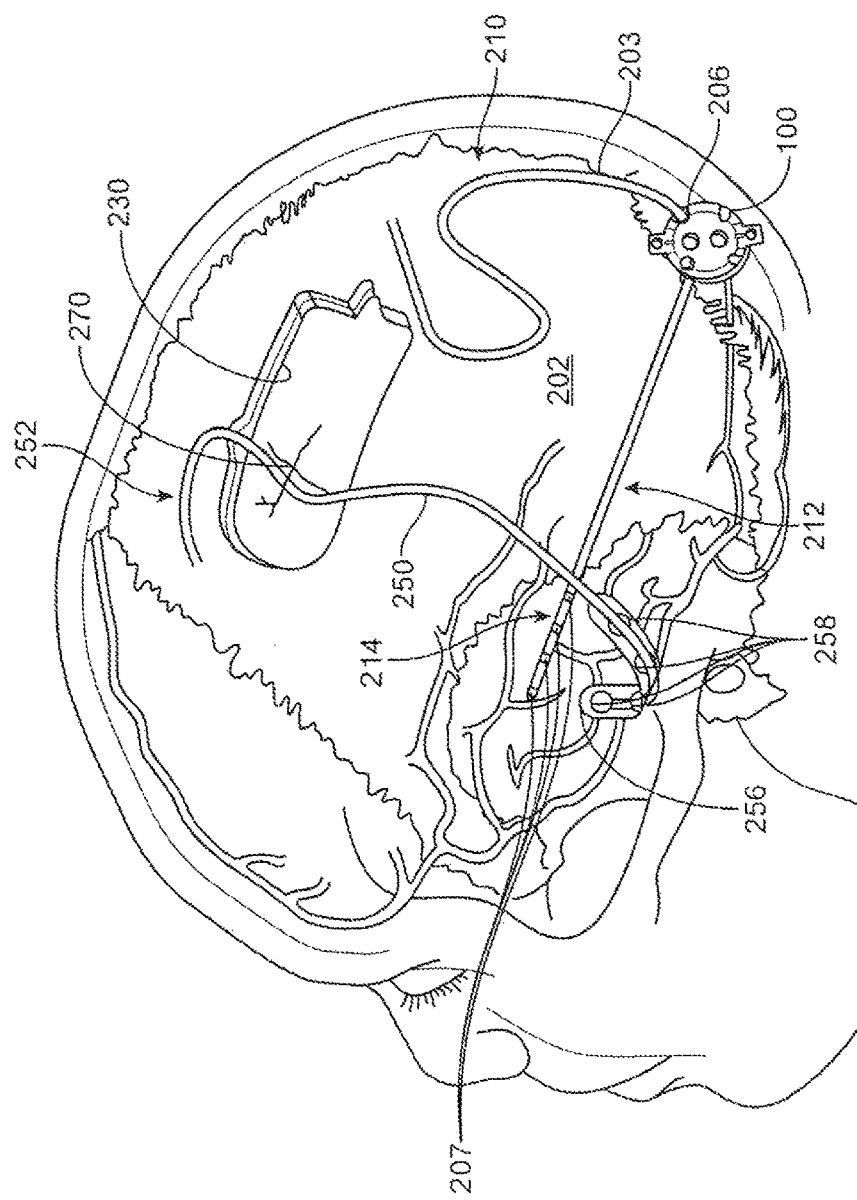
FIG. 2B is a schematic view of an electrode-bearing brain leads, at least one of which has a distal portion thereof implanted in the patient and a proximal portion thereof secured at a burr hole by a burr hole cover.

Referring now to FIG. 2B, a burr hole cover 100 is used to secure a segment of a proximal portion 210 of a deep brain lead 203 in a burr hole formed in a cranium 202 of a patient. More particularly, a distal portion 212 of the deep brain lead 203 is shown implanted in the brain tissue of the patient, and passing through a burr hole in which a burr hole cover 100 is installed. Exteriorly of the patient's skull, the proximal portion 210 of the deep brain lead 203 is shown arranged on top of the patient's skull.

A hole 230 formed has been formed in the patient's cranium 202 which may be intended to receive another medical device, such as an implanted neurostimulator (not shown) to which a proximal end (not shown) of the deep brain lead 203 ultimately may be connected (e.g., for allowing stimulation to be delivered to or physiological activity of the brain to be sensed and/or recorded).

A second brain lead is also shown in FIG. 2B, namely, a cortical strip lead 250. The cortical strip lead 250 has a distal portion that includes a distal strip 256 which contains four disk electrodes 258 that are intended to be implanted so that each rests against a surface or adjacent a surface of the brain. A proximal portion 252 of the cortical strip lead 250 is shown extending exteriorly of the cranial cavity through a stitched-together incision 270 in the patient's scalp rather than through a burr hole or via a burr hole cover. It will be appreciated that a cortical strip lead does not have to be routed as shown in FIG. 2B, rather a proximally-extending portion 252 of a cortical strip lead may be routed through a burr hole as is the case with the deep brain lead 203 shown in FIG. 2B.

Referring again to the deep brain lead 203 of FIG. 2, four ring electrodes 207 are provided at a distal end 214 of the distal portion 212 of the deep brain lead 203. In a method according to an embodiment, a surgeon inserts the distal portion 212 of the brain lead 203 in the patient's brain so that the ring electrodes 207 are in or are adjacent a desired structure or structures or other target in the brain tissue. The surgeon may locate the desired implant site for the electrodes using one or more means such as forms of imaging (e.g., MRI) or microelectrode recordings. The surgeon may manipulate the distal portion 212 of the deep brain lead 203 to the target location(s) using stereotactic equipment and methods or some other suitable technique or approach.

Once the distal end 214 and its associated electrodes 207 are located where the surgeon wants them to chronically remain, the surgeon or one assisting the surgeon grabs (either with fingers or using a surgical instrument or tool) the proximal portion 210 of the deep brain lead 203 that extends exteriorly of the burr hole 200. Next, the surgeon positions the base 110 in the burr hole, secures the segment 206 of the proximal lead portion to be secured by the burr hole cover 100 in the burr hole cover, and then inserts the cap 160 into the base 110 and pushes it down in the direction of the brain to affix the lead segment 206 relative to the burr hole cover 100.

In embodiments, and referring again to FIG. 1A, the user may orient the lead segment 206 in one of a plurality of possible retaining elements 130, such as the four base channels 130 shown in FIGS. 1, 3-5, 7 and FIGS. 13-14. Once the lead segment 206 is oriented in a desired retaining element 130, the user can line the cap 160 up with the base 110 (alignment features may be provided on the base and/or the cap for this purpose), so that the base channel in which a lead segment 206 has been placed can be matched up with a corresponding cut-out 162 on the cap 160. Desirably, the cap 160 is provided with the same number of cap cut-outs 162 as there are retaining channels 132.

After the user has placed the lead segment 206 in a base element 130 and properly aligned the cap 160 relative to the base, the user may engage a locking mechanism configured using features provided on each of the base 110 and the cap 160 to lock the lead segment 206 relative to the burr hole cover 100. The lead segment 206 is thereby restrained, and movement of the distal end 214 of the lead 203 from the location at which it has been implanted in the patient is thereby discouraged.

Figure 12:
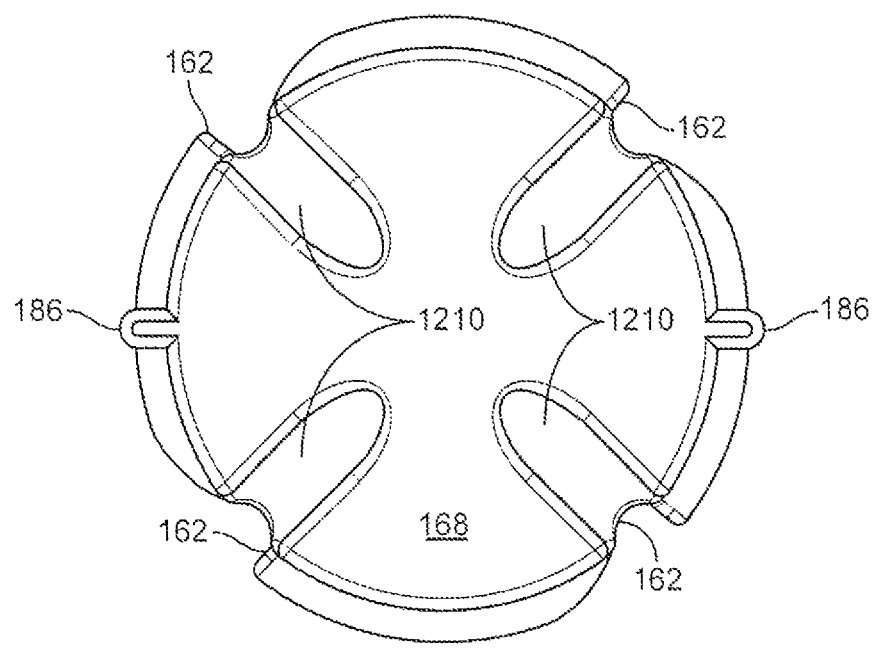
FIG. 12 is a bottom plan view of a cap of a burr hole cover according to an embodiment.

Optionally, the cap 160 is provided with a plurality of guides 1210 (see bottom view of cap in FIG. 12). A guide 1210 is associated with each cap cut-out 162 on a bottom surface 168 of the cap. A guide 1210 associated with the cut-out 162 in which the lead segment 206 is secured will tend to discourage the portion of the lead extending distally from the burr hole from being bent at a sharp angle near the bottom of the burr hole and perhaps from pulling away from its intended implant site during the process of securing the lead in the burr hole cover 100.

It is contemplated that more than one lead segment 206 or portion of other medical device may be secured between the cap and base of a burr hole cover according to the embodiments described herein. For example, if a base 110 is provided with four channels 130 and a cap 160 with four cut-outs 162 corresponding to the four base channels, then the burr hole cover may be used to secure two lead segments 206 and possibly as many as four lead segments 206 (if each channel-and-cut-out combination is occupied by a lead segment).

Depending on the features with which the base 110 is provided, before the distal portion 212 of the lead 203 is implanted in the patient, the base 110 may need to be threaded over the lead 203 so that the lead is passing through the cap-receiving aperture 128 (not shown in FIG. 2) of the base 110.

After the lead 203 is implanted and the burr hole cover 100 is partially or fully installed to secure the lead 203, a proximal end (not shown) of the proximal portion 210 of the lead 203 may be routed to and connected to another implanted device, such as a neurostimulator. Alternatively, a proximal end (not shown) may be connected to a piece of external equipment that can generate a form of neuromodulation to be communicated through the lead and/or monitor and/or record signals sensed from the patient's brain via the lead.

Once the components 110 and 160 of the burr hole cover 100 have been installed (which installation is described more fully below), the distal portion 212 of the lead will be discouraged from moving appreciably relative to the segment 206 of the proximal lead portion 210 that is situated in the burr hole cover 100, even when the proximal portion 210 that extends proximally away from the point of affixation at the burr hole cover 100 is manipulated (for example, when the surgeon attaches a proximal end to another device internally or externally of the patient or when the patient fiddles or fusses with the proximal portion 210 during the time when the lead remains chronically implanted in the patient.)

Figure 4:
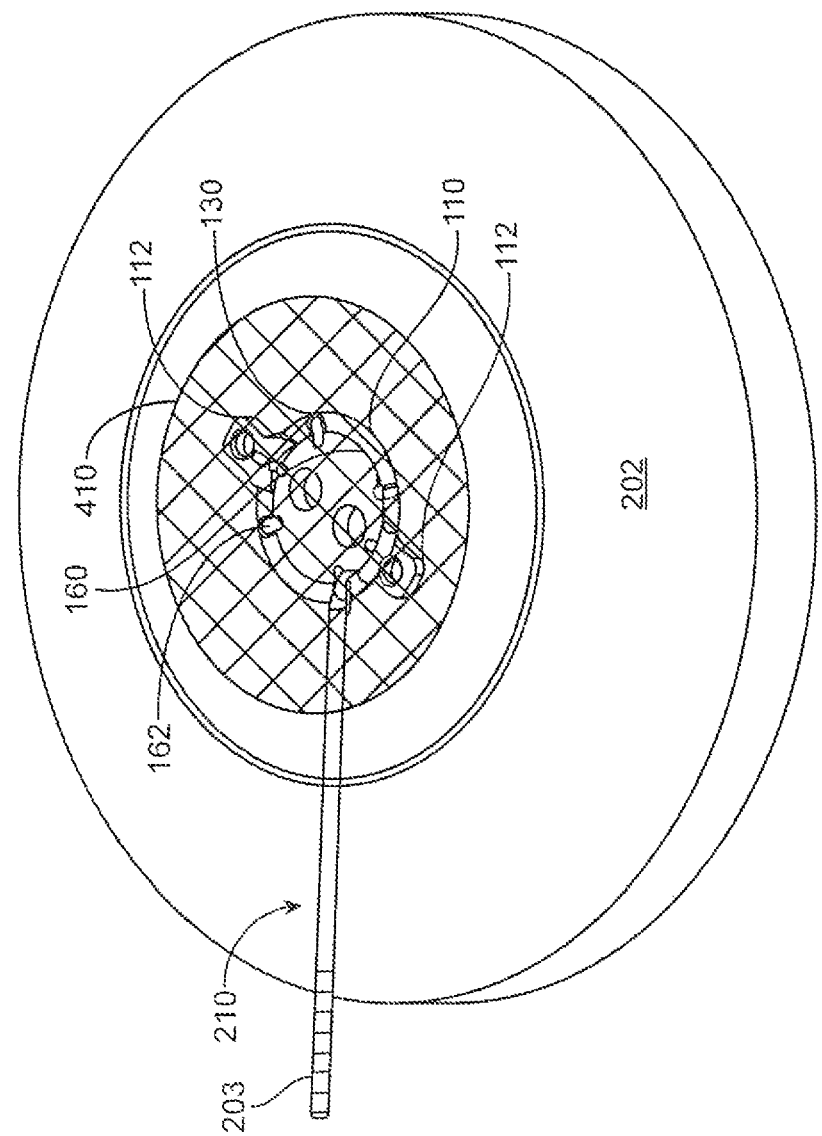
FIG. 4 is the perspective view of FIG. 3 showing an additional feature of an insulator covering the installed burr hole cover.
Figure 5:
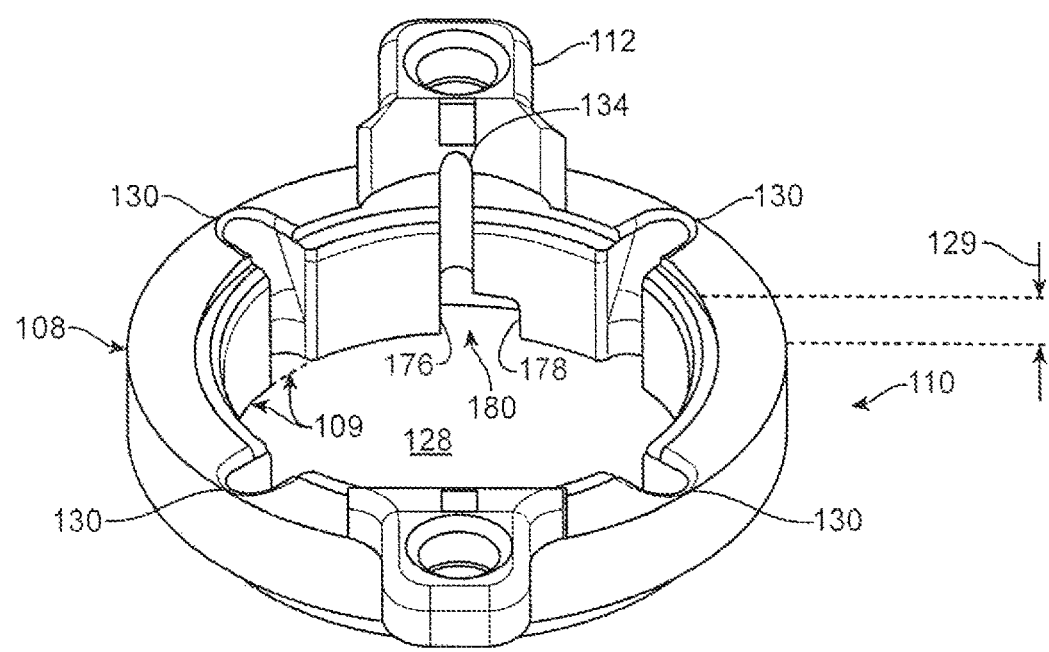
FIG. 5 is a perspective view of a base of a burr hole cover according to an embodiment.

Optionally, after the burr hole cover 100 has been installed and before or after the proximal end of the proximal portion 210 of the lead 203 has been routed to wherever it is to be connected, and referring now to FIG. 4, an insulator 410 may be disposed over the installed burr hole cover 100 to protect some part of the proximally-extending portion 210 of the lead 203 as it exits the burr hole cover 100. The insulator 410 may be formed from a relatively pliant material, such as silicone, and attached to the cranium using screws and/or adhesive or some other means of attachment.

When the lead 203 is intended to remain in place chronically, after the procedure to implant the lead is completed and the burr hole cover 100 is installed, the burr hole cover 100 (or the burr hole cover 100 and insulator 410, if an insulator is used) may be re-covered with the retracted or removed section of scalp or with a prosthetic or synthetic scalp substitute.

When the medical device being secured is an electrode-bearing brain lead such as the lead 203, one or more conductors may be provided in the lead to permit electrical connectivity between the electrodes on the distal end 214 and a lead proximal end (not shown) that ultimately is connected either to another implanted device, such as a neurostimulator, or to an external component not implanted in the patient. If there are multiple conductors in a lead 203, the conductors may be insulated from each other within the body of the lead 203. If the lead 203 (or other medical device) is to be introduced into brain tissue, the lead 203 may be formed from materials that render it more malleable or floppy than stiff, for example, to minimize the likelihood that the lead will interfere with the tissue in which (or against which) it is implanted or otherwise cause trauma at and around the implant site. In a case where a lead 203 is not inherently stiff, the lead 203 may be provided with a lumen or cavity that extends almost all of the way through or just partially through the body of the lead to accommodate a stiffener, such as a stylet, which can remain in place during the procedure to implant the lead and thereafter can be removed.

If the medical device to be secured with a burr hole cover includes conductors, then the risk of compromising the conductors (e.g., breaking or overstressing the conductors) either during or subsequent to installation of the burr hole cover desirably should be minimized. Similarly, if the medical device is a lead that is not inherently stiff but has its stiffness supplemented with a stiffener such as a stylet that is ultimately intended to be withdrawn and removed from the lead, then the burr hole cover will need to be adequate to affix the lead in the vicinity of the burr hole with the stylet absent from the lead body. In some cases, it may be desirably to affix the lead with the burr hole cover before withdrawing the stylet (for example, to minimize the likelihood that the distal portion of the lead will be dislodged from the intended target area during the affixation process). In other cases, it may be desirable to affix the lead with the burr hole cover after the stylet has been removed from the lead body (for example, to avoid the possibility that an installed or partially installed burr hole cover will interfere with withdrawing the stylet from the lead body or will result in unintended movement of the distal portion of the lead). Depending on the features with which the burr hole cover 100 is provided, any stylet may need to be withdrawn proximally from the lead past the segment 206 that is to be secured in the burr hole cover 100 before the segment can be secured.

In addition to the nature of the medical device (e.g., lead with conductors extending therethrough or some other type of medical instrument such as a catheter) and the relative stiffness of the medical device (e.g., whether it is stiff or has a removable stiffener), another criterion for selecting a burr hole cover is the degree of security desired at the segment 206 of the proximal lead portion 210 to be situated in the burr hole cover 100. For example, in some applications, it may be undesirable for the distal portion 212 of a lead 203 to move more than a fraction of an inch once the distal end 214 has been positioned at a target area. This might be the case where one or more electrodes (such as one or more of the electrodes 207) are intended to remain at or near a relatively small physical target in the brain (e.g., the STN). In other applications, it may be acceptable for the distal end 214 of the lead 203 to shift or migrate more over the period of time in which the lead remains implanted in the patient (e.g., when electrodes are being used to stimulate or sense from a broader physical target area or to stimulate or sense at some point in a functional pathway (such as a known or suspected brain circuit), as contrasted to a physical structure). In some applications under investigation that use an implanted neurostimulator together with one or more implanted electrode-bearing leads to treat epilepsy, more potential movement of the distal end 214 of the lead 203 may be tolerable than in other applications, such as an application using deep brain stimulation to treat the symptoms of a movement disorder.

In still other circumstances, one factor in selecting a burr hole cover to use for a particular patient may be the profile of the burr hole cover 100, that is, the extent to which the burr hole cover will protrude from the patient's cranium 202 once it has been installed. The profile consideration may be directly or indirectly related to the nature of the medical device the burr hole cover 100 is being used to secure. For example, a user may want to avoid causing sharp bends or angles in a lead with conductors running through it to minimize the risk of compromising the function of the lead or any electrodes with which the lead is associated. The profile of a burr hole cover may help the user to minimize such sharp bends. The profile of a burr hole cover may also be relevant for aesthetic reasons, for example, so that the burr hole cover cannot readily be perceived by others (for example, as contrasted to a burr hole cover that produces a noticeable bump under the scalp in a bald patient). Finally, there may be practical reasons that drive selection of a burr hole cover with a particular profile: for example, patients may be more likely to "fiddle" with a higher profile burr hole cover and any associated lead(s) or other medical devices that are secured by it simply because the patient is likely to notice the burr hole cover more.

Referring now to FIGS. 1-15, embodiments of a burr hole cover 100 are characterized by a base 110. The base 110 is provided to be generally circular in shape with a circumference that is slightly less than the circumference of the burr hole 200 with which the burr hole cover 100 is to be used. More particularly, since in use the base 110 of the burr hole cover 100 will be inserted well into the burr hole 200, the circumference of the base 110 should not exceed the likely circumference of the burr hole with which it is to be used. Burr holes 200 are often drilled with special drill bits which are configured to form a fenestration in the cranial bone with predetermined approximate dimensions (e.g., a 14 mm diameter circular hole). Thus, in embodiments of the burr hole cover 100 described here, the dimensions of the base 110 and cap 160 components for a given burr hole cover 100 may be selected to be slightly smaller than the dimensions of standard-sized burr holes, so that a variety of commonly-sized burr holes may be accommodated.

Figure 6:
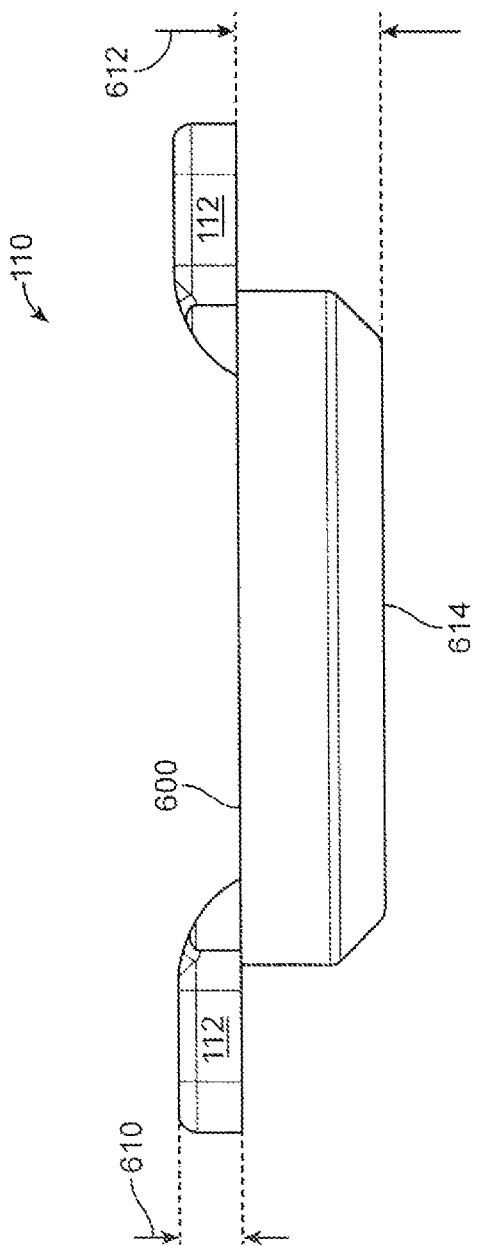
FIG. 6 is a side elevational view of the base of FIG. 5.
Figure 7:
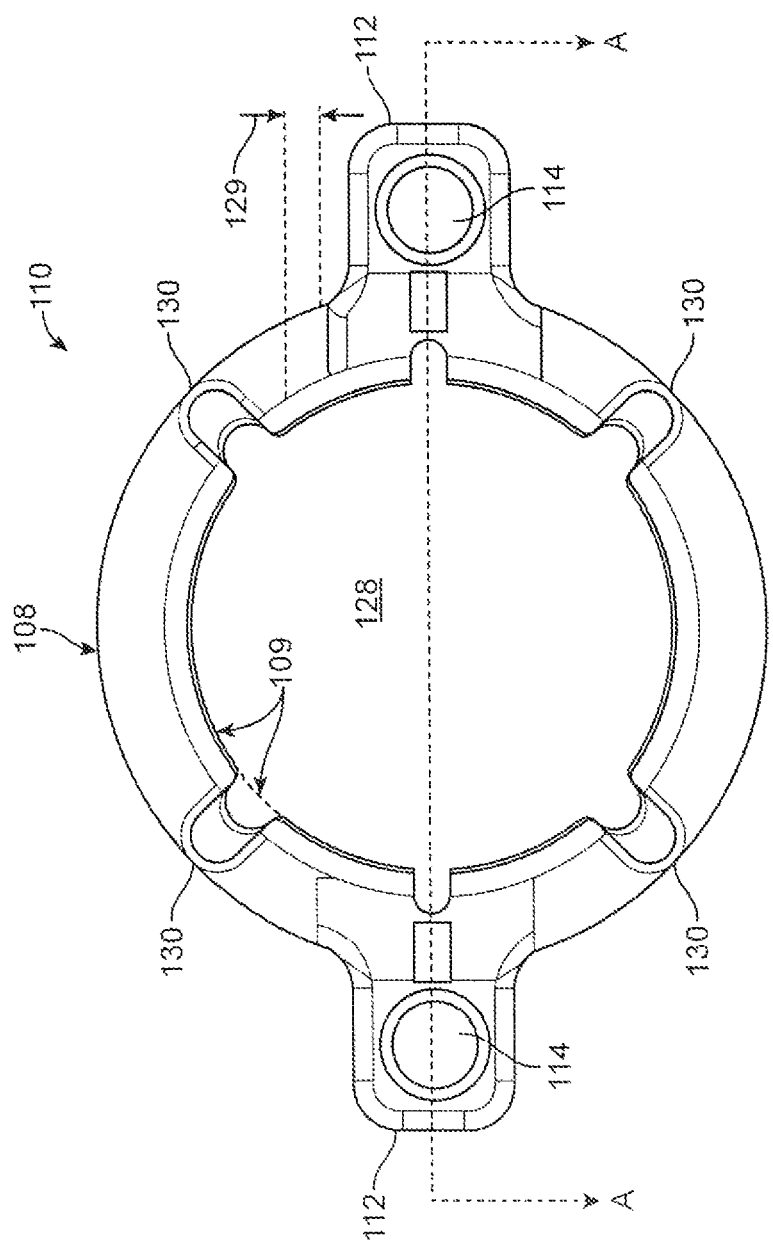
FIG. 7 is a top plan view of the base a burr hole cover according to an embodiment.
Figure 8:
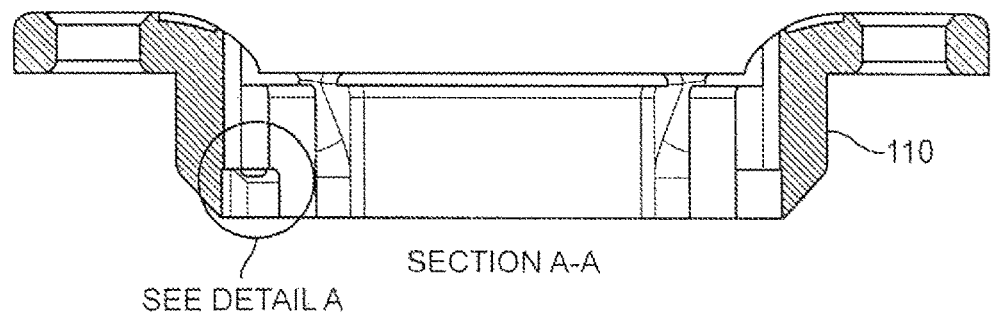
FIG. 8 is a sectional view taken along the line A-A of FIG. 7.
Figure 9:
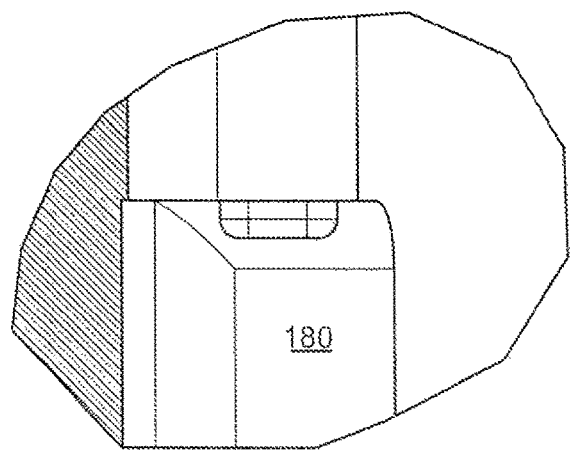
FIG. 9 is an exploded view of a portion of the sectional view of FIG. 8.

The base 110 is provided with a pair of pads 112 extending out from the circumference of the base. Each pad 112 may be provided with an aperture 114 configured to receive a bone-attaching element (such as the bone screws 1310 shown in FIGS. 13A and 14A) with which to attach the base 110 to the patient's cranium 202. As best shown in FIG. 6, each pad 112 may be slightly offset by a height or distance 610 measured from a top surface 600 of the base 110 (i.e. the surface of the base that will face away from the brain when the base is installed in the burr hole 200). The offset distance 610 is provided so that the entirety of the base 110 except for the pads 112 for attaching the base to the cranium 202 can be situated in a plane that is at or below the top surface of the burr hole 200. With the base 110 recessed in the burr hole 200 in this manner, the burr hole cover 100 essentially has no profile above the burr hole save for pads 112.

In other embodiments, the burr hole cover 100 may be provided with features other than the pads 112 for securing the base 110 and/or the cap 160 to the cranium 202. Such features may include elements configured to allow the base to be anchored to the interior of the burr hole 200, such that no part of the base 110 is configured to extend above the exterior-facing surface of the burr hole 200.

Referring especially to FIGS. 2A and 6, the base 110 is characterized by a depth or thickness 612 that is selected to be equal to or less than the burr hole depth 220. The base thickness 612 corresponds to the distance traversed between the top surface 600 of the base 110 and a bottom surface 614 (i.e., the surface intended to face interiorly of the burr hole when the burr hole cover is installed). As the base 110 is configured to seat interiorly of the burr hole 200 formed in the patient (except for the pads 112, if pads 112 are provided), when the base 110 is installed, the thickness 612 will traverse some or all of the distance between the outermost surface of the cranium and the innermost surface of the cranium (i.e., the surface of the cranial bone closest to the brain). Thus, the base thickness 612 may be provided with a dimension that generally corresponds to the thickness of the average person's cranial bone in a given area of the skull (or, put another way, to the average burr hole cover depth 220). Preferably, the thickness 612 will be selected so that when the burr hole cover 100 is completely installed, no component of the burr hole cover 100, including the base 110 or the cap 160, will extend further in towards the brain by a distance greater than the thickness of the cranial bone where the burr hole 200 has been formed. Since every patient's skull thickness may be different, and burr holes may be drilled in different parts of a patient's skull, the thickness 612 should be selected to suit multiple possible cranial bone thicknesses. Alternatively, bases with a variety of thicknesses may be provided in order to accommodate different patient's skull thicknesses.

The base 110 is characterized by an outer perimeter 108 along the circumference thereof and is provided with a cap-receiving aperture 128 circumscribed by an inner perimeter 109. The base 110 is characterized by a width 129 corresponding to the distance the base traverses between the outer perimeter 108 and the inner perimeter 109. The base 110 may be selected to be wide enough to provide stability to the burr hole cover 100, but not so wide as to encroach too significantly upon the amount of working space. That is, the space defined by the cap-receiving aperture 128 is the space in which a user is able to manipulate the lead or other medical device to be secured by the burr hole cover to, for example, orient a lead segment 206 in one of the retaining elements 130. The base should be just wide enough to stably anchor the burr hole cover assembly in the burr hole so that the user has the maximum possible room to maneuver the lead during the installation process.

In some embodiments, the base 110 may be provided with ridges or threads (not shown) on an outer surface thereof to encourage the base 110 to engage with a surface of the cranial bone exposed by the drilling of the burr hole and therefore further stabilize the base 110 relative to the burr hole 200.

The base 110 is provided with a plurality of retaining elements 130 and at least two alignment features 134. In some embodiments, the shape and contour of each retaining element 130 is configured to cooperate with a corresponding cut-out 162 provided on the cap 160, so that when a retaining element 130 such as a base channel of the base 110 is aligned with a cap cut-out 162 of the cap 160, the mating of the base channel 130 and the cut-out 162 forms an approximately cylindrical or elliptical aperture 310 through the base 110 (see, e.g., FIG. 3 and FIGS. 13A-13B). Desirably, the diameter of the mated aperture 310 is large enough to allow the medical device the burr hole cover is designed to secure (e.g., a cylindrical brain lead) to move freely within the mated aperture 310.

Figure 1B:
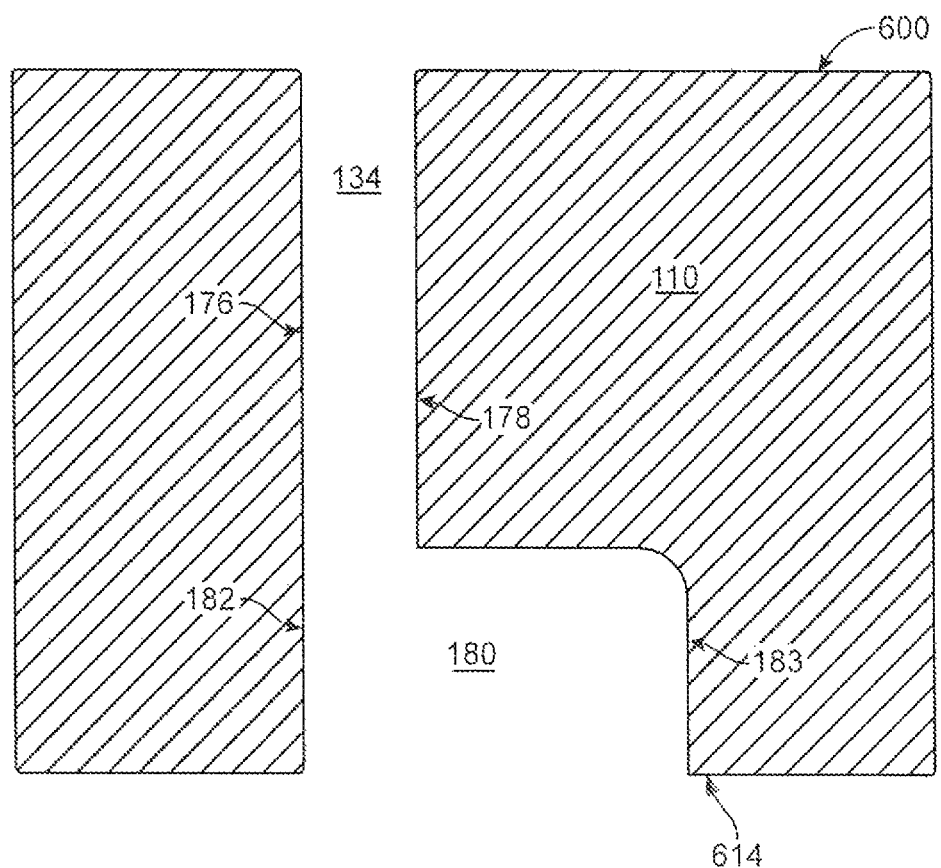
FIG. 1B is a detail of a portion of a base of the burr hole cover shown in FIG. 1A.
Figure 13A:
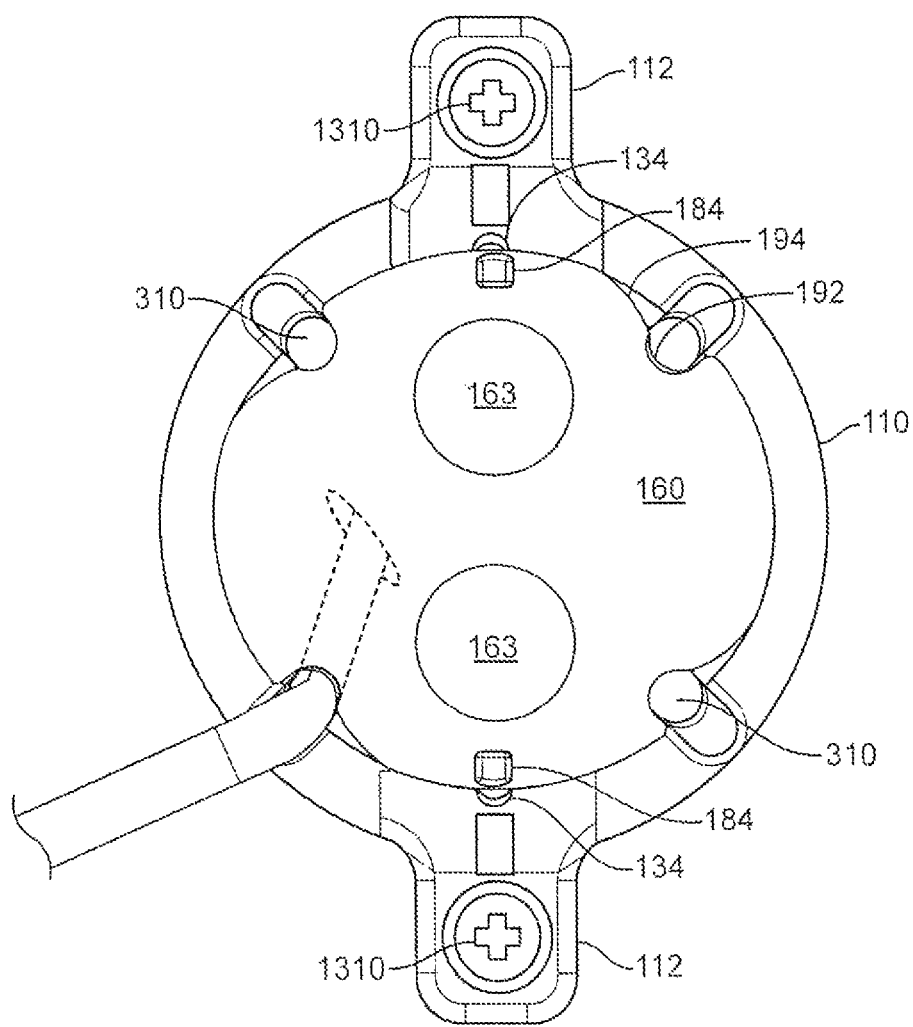
FIG. 13A and FIG. 13B are top and bottom views, respectively, of a burr hole cover assembly according to embodiments in an unlocked position.
Figure 13B:
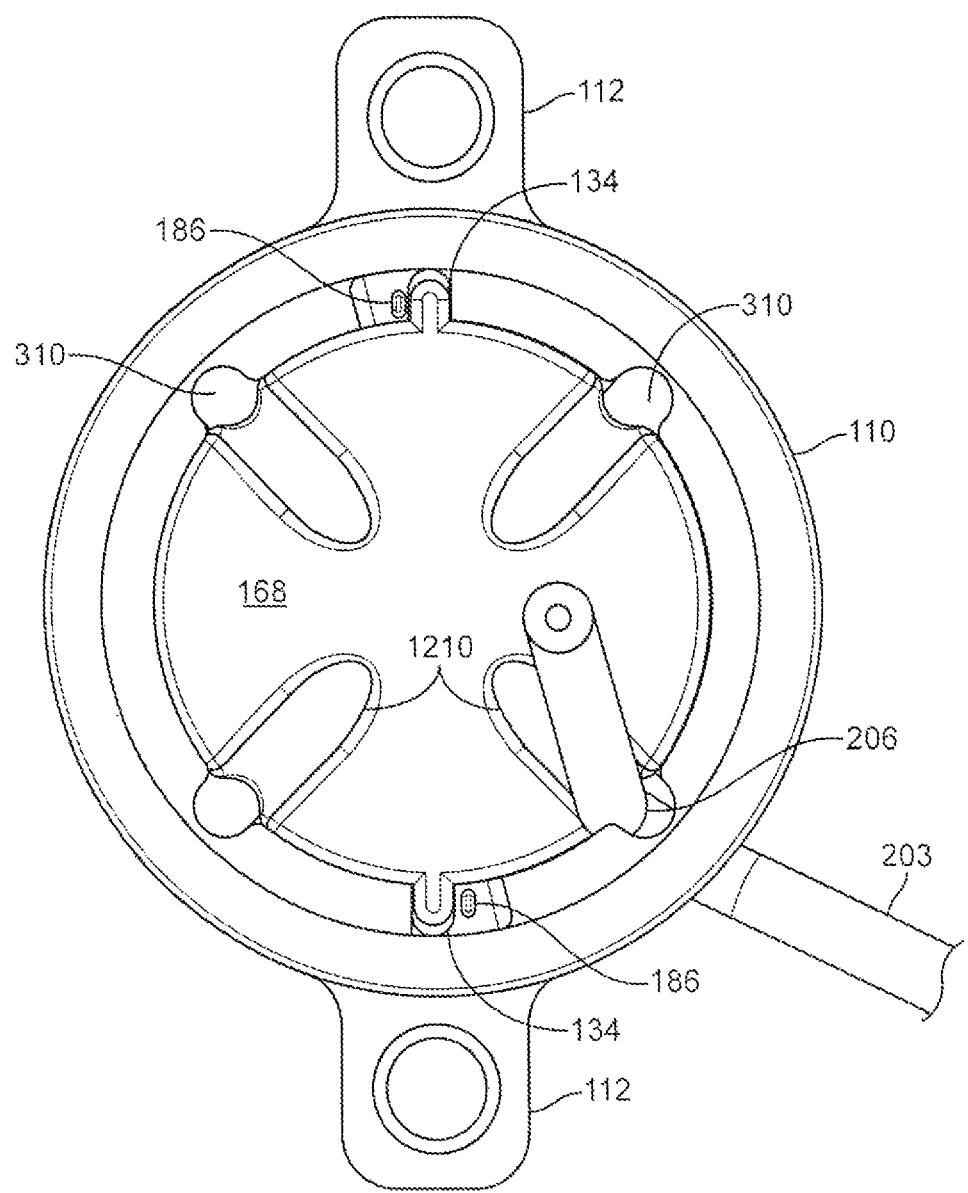

The alignment features 134 of the base 110 are provided to assist a user in placing the cap 160 in an initial position (as shown in FIGS. 13A-13B) relative to a base 110 that has been previously situated in a burr hole 200 (as for, by example, using bone screws in the pad apertures 114). The alignment features 134 may comprise a pair of slots that are disposed opposite each other on an inner surface of the base 110. Referring now to FIG. 1B, each slot 134 may be defined by a left edge 176 and a right edge 178 and extends from the top surface 600 to the bottom surface 614 of the base 110. Near the bottom surface 614, each slot 134 widens into a square or rectangularly-shaped locking pocket 180 of the base 110. In the embodiments shown, each slot 134 widens into a locking pocket 180 that extends from the left edge 176 of the slot, owing to the manner in which the locking mechanism for these embodiments is configured, as is further described below. Each locking pocket 180 may be characterized by a near edge 182 which is common with a portion of the left edge 176 the relevant slot 134 and a far edge 183.

The base 110 may be formed from a material that is relatively rigid such as a plastic or polymer (e.g., poly-ether-ether-ketone or PEEK). The material should be non-toxic in the event in comes into contact with bodily fluids or tissue and should be long lasting when implanted in a cranial burr hole. The material may be clear or opaque so that the contours of the burr hole 200 may be perceived while the base 110 is being situated. Alternatively, the base 110 may be formed from a more resilient or pliable material, such as silicone rubber. Such a more resilient material may assist in managing the stresses and strains placed on the medical device both during and after the burr hole cover is installed to fix a segment of the device relative to the burr hole.

Figure 10:
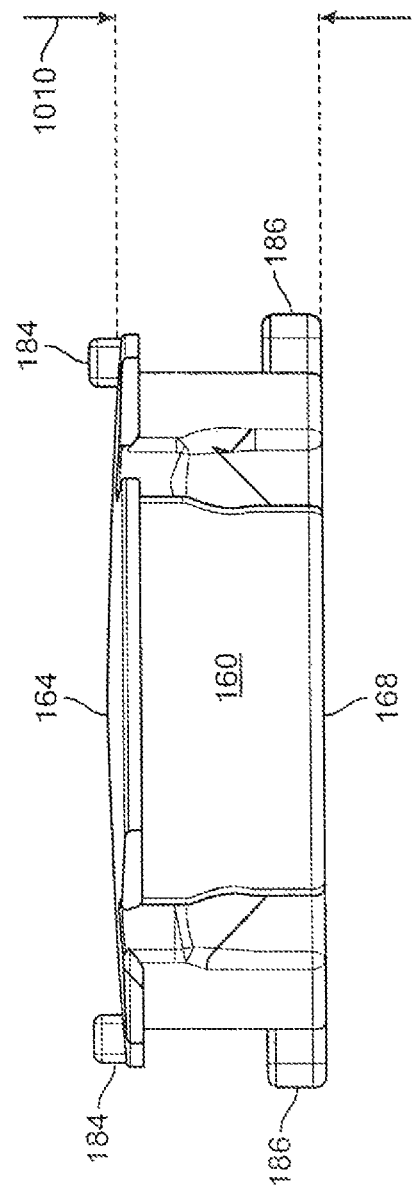
FIG. 10 is a side elevational view of a cap of a burr hole cover according to an embodiment.
Figure 11:
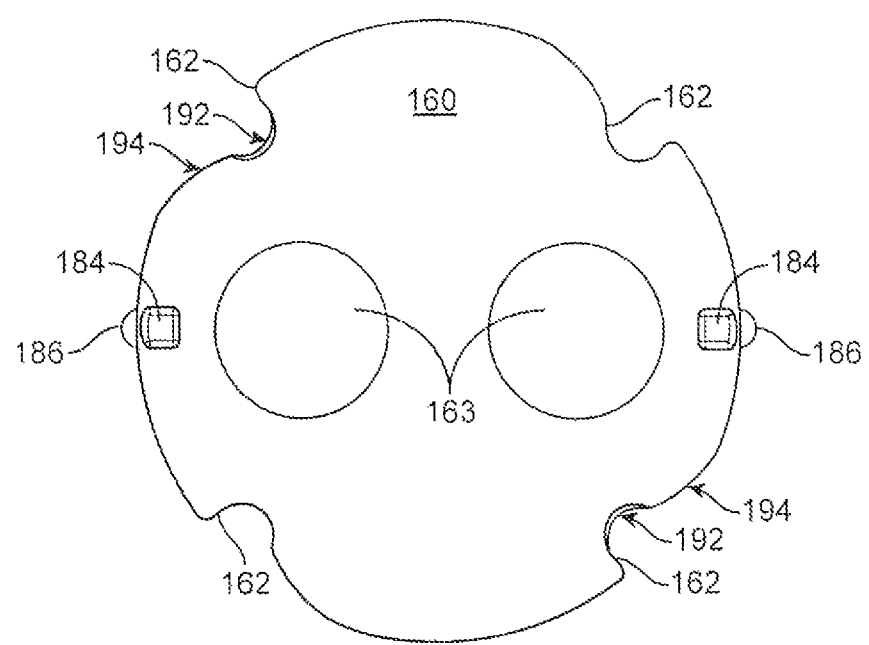
FIG. 11 is a top plan view of a cap of burr hole cover according to an embodiment.

Referring now especially to FIG. 1A and FIGS. 10-11, a cap 160 according to embodiments is further described. The cap 160 is characterized by a top surface 164 and a bottom surface 168, a plurality of cut-outs 162 extending through the cap top surface 164 to the cap bottom surface 168 and each configured to mate with a retaining element 130 of the base 110, a pair of alignment features 184 configured to align with a corresponding pair of alignment features 134 in the base, a pair of locking features 186, and a plurality of guides 1210, such as lead guides, provided in the cap bottom surface 168.

The cap 160 is designed to fit entirely within the circumference of the base 110, such that all parts of the cap rest within the bounds of the base outer perimeter 108 when the cap is fitted into the base. Similar to the base thickness or depth 612, and as illustrated in FIG. 10, the cap 160 is characterized by a thickness 1010 measured as a distance between the cap top surface 164 and the cap bottom surface 168. The cap thickness 1010 is desirably designed so that, when the cap 160 is fitted into the base 110, the top surface 164 of the cap will be approximately in the same plane of the top surface of the base 600. Put another way, the burr hole cover 100 when fully assembled with the segment of the medical device it is meant to secure will be entirely recessed within the burr hole 200 save for any bone-attaching pads 112 offset above and extending away from the base top surface 600. Alternatively, the cap thickness 1010 is specified so that when the cap 160 is fitted into the base 110, the cap top surface 164 will not sit appreciably higher than the top 215 of the burr hole 200 itself.

Each cap cut-out 162 is provided with a semi-circular indentation 192 and a radius 194. Each cut-out 162 is configured to match up with a corresponding retaining element 130 in the base 110 (such as a base channel) to form a mated aperture 310. As alluded to above, the diameter of the mated aperture 310 desirably is slightly greater than the diameter of the medical device (e.g., a lead) the burr hole cover 100 is used to secure. (It will be appreciated that in alternative embodiments, the shape of an aperture 310 formed by the mating of a retaining element 130 in the base and a cut-out 162 in the cap may be different, such as if the medical device to be secured with the burr hole cover is not cylindrical as typically is a brain lead.)

Each alignment feature 184 of the cap 160 is provided in the same vertical plane as a corresponding cap locking feature 186. As can be best seen in FIGS. 1A, 10, and 11, the alignment features 184 are provided as tabs that extend outwardly and upwardly from a circumference of the cap 160 near the top surface 164 of the cap. The locking features 186 are provided as locking protrusions that extend outwardly from the circumference of the cap 160 near the bottom surface 168 of the cap. Each alignment tab 184 and its vertically aligned locking protrusion 186 are configured to slide within a corresponding slot 134 of the base 110. Therefore, neither the cap alignment feature 184 nor the cap locking feature 186 is provided with a dimension that would preclude it from fitting in the corresponding alignment feature 134 in the base 110. For example, neither the cap alignment tabs 184 nor the cap locking protrusions 186 are provided to be wider than the narrowest dimension of the corresponding alignment slot 134 in the base 110.

When the cap 160 is positioned relative to the base 110 so that both of the alignment tabs 184 are lined up with the corresponding slots 134 in the base 110, then the cut-outs 162 in the cap 160 will be mated with the corresponding channels 130 in the base, including the base channel 130 in which the user has situated the lead segment 206.

To lock the cap 160 relative to the base 110 and to thereby secure the lead segment 206, the user rotates the cap 162 in the direction of the radius 194 of the cut-out 162. In the embodiments shown in the figures, this direction is clockwise or to the right. When the cap 160 is rotated relative to the base 110, the cut-out radii 194 will slide to the right, and the cut-out radius 194 in the mated aperture 310 in which the lead segment 206 has been situated will be pressed into contact with the base. Also when the cap 160 is rotated, each locking protrusion 186 will slide into its corresponding locking pocket 180 in the base. When the cap 160 is rotated so far that the locking protrusions 186 abut the far edges 183 of the locking pockets 180, the far edges 183 of the locking pockets will act to resist any further rotation. Thus, when the locking protrusions have been stopped by the far edges 183 of the locking pockets, the cap 160 will be at its final position within the base 110 and the lead segment 206 will be locked into place in the burr hole cover 100.

It will be appreciated that a cap and base according to embodiments may be provided with elements and features, including base retaining elements and cap cut-outs, base alignment slots and cap alignment tabs, and base locking pockets and cap locking protrusions, that allow relative movement of the cap and base in other directions to secure a portion of a medical device in the burr hole cover.

Figure 15:
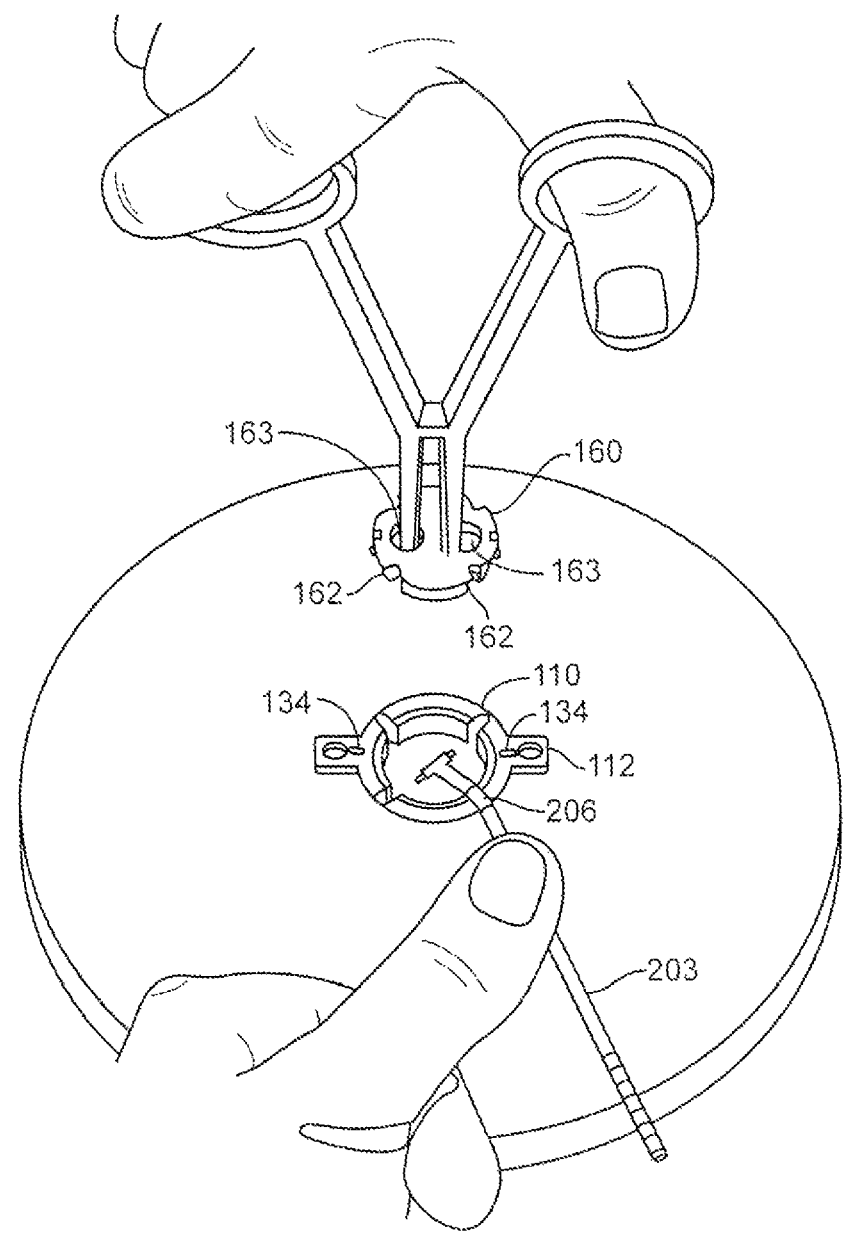
FIG. 15 is a schematic view of a user manipulating a cap of a burr hole cover according to embodiments relative to a retainer.

The cap top surface 164 preferably is provided with one or more recessions 163 for receiving a surgical tool (preferably a common surgical tool such as forceps or tweezers) which a user can rely upon to hold and manipulate the cap 160 during a process of installing or uninstalling the cap in the burr hole cover 100 (see also FIG. 15). Alternatively, the cap 160 may be designed for use with a custom installation tool, in which case the features provided in the cap 160 for facilitating installation will be suitable for use with, and perhaps unique to, the custom installation tool. (It will be appreciated that features to improve the ease with which the surgeon can manipulate the cap relative to the other components of the burr hole cover may also be relied upon to remove the cap, for example, in the process of removing or replacing a previously implanted lead that has been secured with the burr hole cover.)

As with the base 110, the cap 160 may be formed from a material that is relatively rigid such as a plastic or polymer (e.g., poly-ether-ether-ketone or PEEK). The material should be non-toxic in the event it comes into contact with bodily fluids or tissue and should be long lasting when implanted in a cranial burr hole. The material may be clear or opaque so that, for example, the lead segment 206 and the portion of the lead extending distally of the lead segment 206 may be perceived by the user while the cap 160 is aligned and locked into position in the base 110 and thereafter. Alternatively, the cap 160 may be formed from a more resilient or pliable material, such as silicone rubber. Such a more resilient material may assist in managing the stresses and strains placed on the medical device both during and after the burr hole cover is installed to fix a segment of the device relative to the burr hole. For example, silicone rubber may be less likely to pinch a portion of a lead against the burr hole cover in a manner that comprises the lead's functionality.

It is noted that the surfaces that characterize the various elements and features of the base 110 and cap 160 that are designed to contact a portion of the lead or other medical device with which the burr hole cover 100 is to be used collectively are configured to minimize the stresses placed on any lead segment 206 (or segment of another medical device) that may be secured by the burr hole cover 100 after it is installed, and, for that matter, the stresses placed on other parts of the lead 203 (such as the proximal portion where the lead exits the burr hole cover at the skull). For example, the portion of the lead that is captured in the burr hole cover 100 is relatively small compared to the overall length of the lead, so a relatively small portion of the lead is subjected to stress within the burr hole cover.

Referring now primarily to FIGS. 13-15, a method of using a burr hole cover according to some embodiments will be described. A lead 203 (or other medical instrument such as a catheter) may be partially implanted in the patient so that a distal portion of the lead 212 (or other medical instrument) extends distally from the burr hole 200 towards and/or into the patient's brain (see, e.g., the direction represented by the arrow E in FIG. 3) and a proximal portion 210 of the lead (or other medical instrument) extends proximally from the burr hole away from the patient's brain (see, e.g., the direction represented by the arrow F in FIG. 3).

By the time the lead is implanted, the base 110 may previously have been situated at the location of the burr hole 204 so that the lead 203 is passing through the cap-receiving aperture 128. If the base 110 is provided with pads 112 for attaching the base 110 to the cranial bone, then the base 110 can be secured to the patient's cranium 202 using bone screws or other appropriate bone-attaching elements. Depending on the configuration of the base 110, it may be secured to the cranium 202 by other or additional means, such as an adhesive. Alternatively, if the base 110 is provided with a feature for slipping the base 110 around a lead 203 (e.g., a slit provided in the base (not shown in the figures)), then the base 110 can be situated at the location of the burr hole even after the lead has been implanted and a portion of the implanted lead is extending proximally out of the burr hole.

When the user is placing the base 110 in the burr hole 200, the user can situate the base 110 so that any retaining elements 130 are oriented in a particular direction relative to the patient's cranium and any other implanted or external device to which the implanted lead 203 is to be connected.

The base 110 is designed to be recessed in the burr hole 200. The user may situate the base 110 inside the burr hole using his or her fingers or an appropriate surgical tool. If the base 110 is provided with pads 112 that are vertical offset from and extend away from the top surface 600 of the base 110, then the pads 112 may assist in preventing the base from inadvertently passing all the way through the burr hole and into the cranial cavity.

Depending on where the user wants the proximal portion 210 of the lead 203 to ultimately be located, e.g., dressed out of the burr hole in an anterior direction (such as towards the patient's nose) or dressed out of the burr hole in a posterior direction (such as towards the patient's back), the user can selected one of the base channels 130 in which to situate the lead segment 206.

When the surgeon is ready to position the lead segment 206 in the base 110, if the lead 203 has been provided with a stiffener such as a stylet which has not yet been removed, then the stiffener desirably is removed at this point. Then, once the user has selected a base channel 130 to use, the surgeon may move the lead 203 around in the working space defined by the cap-receiving aperture 128 until the surgeon has decided upon a base channel 130 in which to situate a proximal portion 210 of the lead at the burr hole, i.e., lead segment 206. Once the lead segment 206 is situated in a desired channel 130, the surgeon can then hold (or have one assisting hold) the proximally-extending portion 210 of the lead 203 out of the way while the surgeon positions the cap 160 relative to the base 110. In embodiments in which the channel is not characterized by a diameter that is smaller than the diameter of the lead 203, the lead segment 206 will be simply resting in the selected channel 130 at this stage, and not be secured there by reason of a press- or friction-fit.

After the base 110 is installed in the burr hole 200 and the lead segment 206 situated in a base channel 130, the user positions the cap 160 over the cap-receiving aperture 128 and aligns the alignment tabs 184 of the cap 160 with the alignment slots 134 of the base 110. FIGS. 13A and 13B are top and bottom views, respectively, of the cap 160 and base 110 in this initial, unlocked position with the cap alignment tabs 184 lined up with the base slots 134. The surgeon may accomplish placing the cap 160 in this initial position relative to the base 110 by using forceps placed in the cap recessions 163 to grab and hold the cap 160 while the cap is being manipulated relative to the base 110 (see FIG. 15).

Because the cap locking protrusions 186 are in the same vertical plane as the cap alignment tabs 184, when the cap alignment tabs 184 are aligned with the base slots 134 and the cap 160 is pressed into the base 110, the cap locking protrusions 186 near the bottom surface 168 of the cap 160 will slide into the slots 134 toward the bottom surface 614 of the base. Each cap cut-out 162 will match up with its corresponding channel 130 in the base 110 to form a mated aperture 310, and one of the mated apertures so formed will contain the lead segment 206.

The guides 1210 provided in the cap bottom surface 168 encourage the portion of the lead extending distally of the lead segment 206 to maintain a gentle curve or bend throughout the time the cap is being manipulated relative to the base 110. More particularly, the guide 169 associated with the base channel 130 and cap cut-out 162 that will be relied upon to secure the lead in the burr hole cover 100 may tend to discourage sharp angles in the lead and/or tugging or pulling on the lead that might move the distal end of the lead from its intended implant location.

Figure 14A:
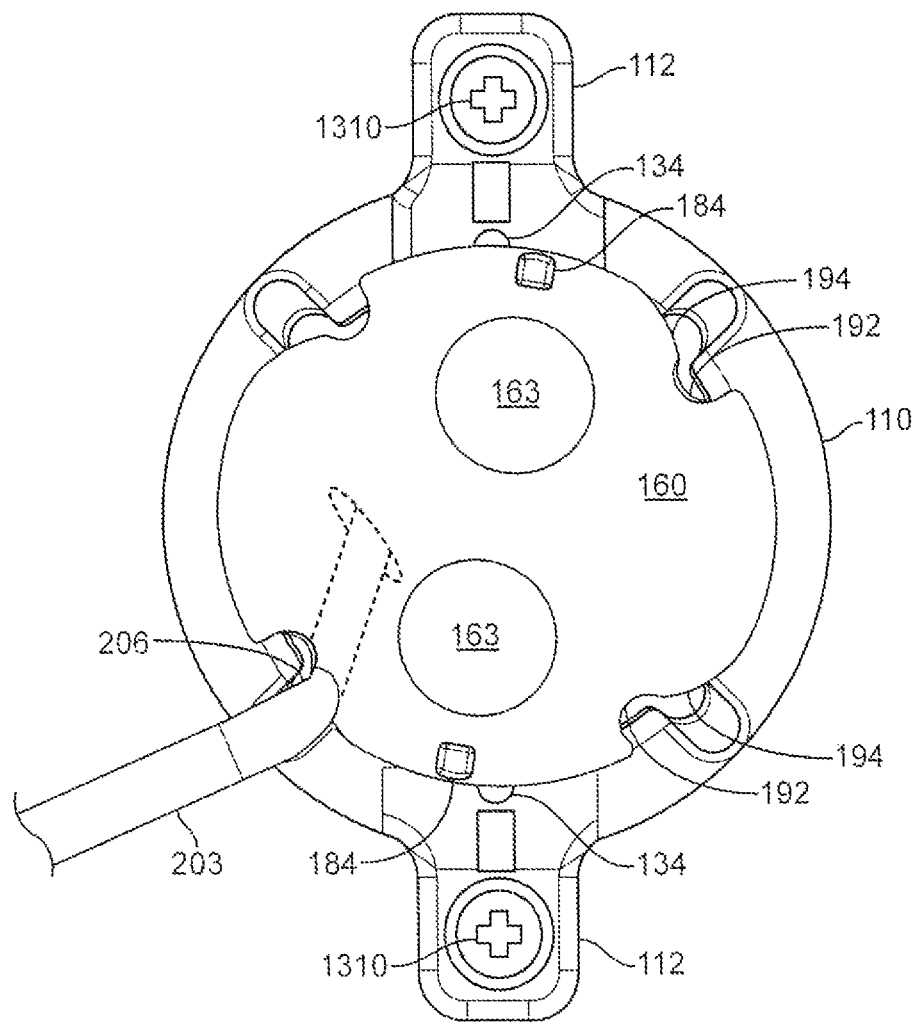
FIGS. 14A and 14B are top and bottom views, respectively, of a burr hole cover assembly according to embodiments in a locked position.
Figure 14B:
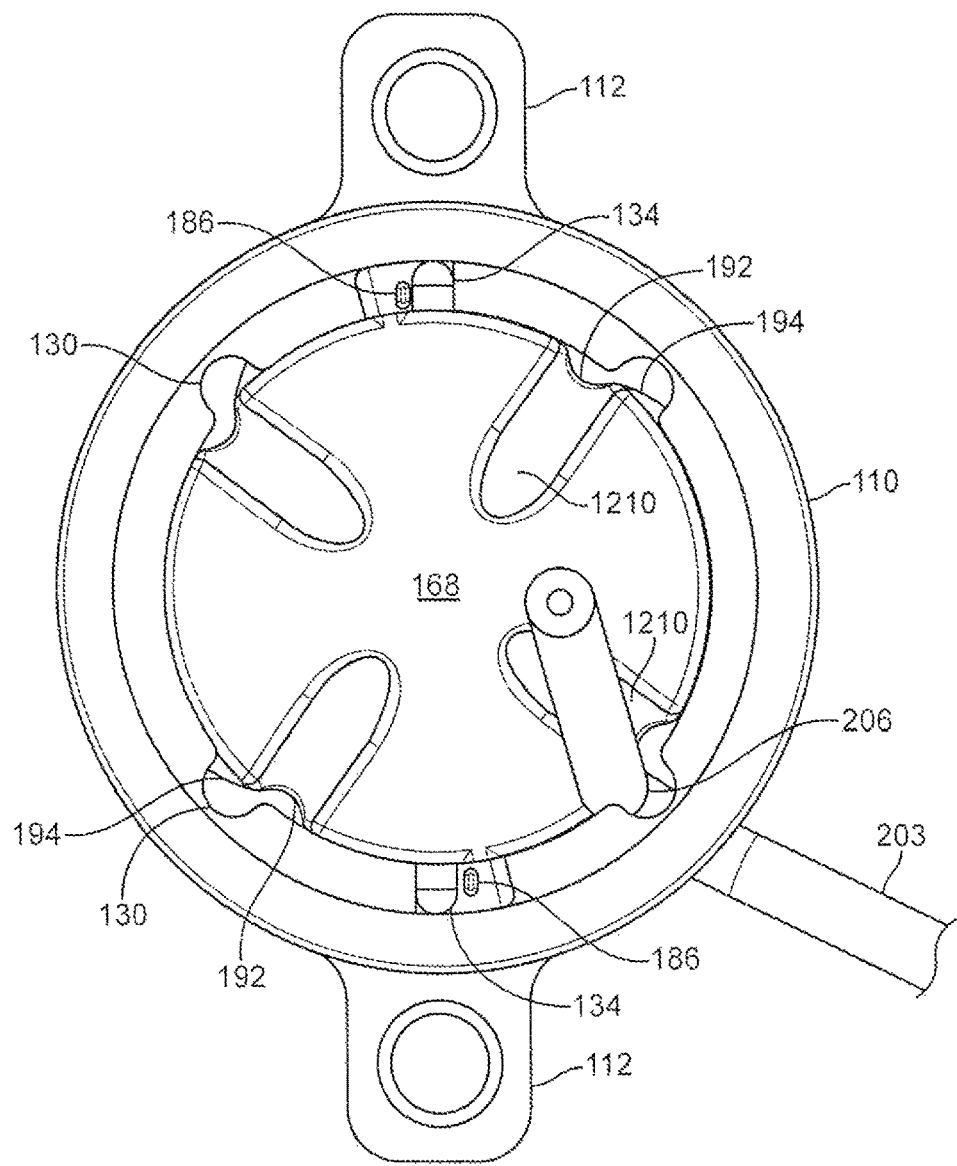

To move the cap 160 into its final position relative to the base 110, the user rotates the cap 160 (still using the forceps in the cap recessions 163 if provided) in a clockwise direction. When the cap 160 rotates to the right, the radii 194 of the cap cut-outs 162 will move into the space defined by each base channel 130. FIGS. 14A and 14B are top and bottom views, respectively, of the burr hole cover with the cap in its final, locked position relative to the base, i.e., with the cap rotated to the right. This rotational movement of the cap 160 after aligning it with the base 110 will cause the lead segment 206 in the base channel that contains it to be pressed between surfaces of the cap 160 and the base 110. The same rotational movement will cause the locking protrusions 186 near the bottom surface 168 of the cap 160 to move into their corresponding locking pockets 180 near the bottom surface 614 of the base 110. When each locking protrusion 186 reaches the far edge 183 of the locking pocket 180 of the base 110, then any further rotation of the cap 160 relative to the base 110 will be resisted in either direction. That is, further rotation in the clockwise direction will be resisted because the stops represented by the cap locking protrusions 186 reaching the far edges 183 of their respective base locking pockets 180 will have been encountered. Rotation back in the counterclockwise direction will be resisted because the cap locking protrusions 186 are now situated in their respective base locking pockets 180. Accordingly, the lead segment 206 at this point will be secured in the burr hole cover 100.

The surgeon may now dress the portion of the lead extending proximally of the burr hole cover 100 in any desired manner. Because the top surface 164 of the cap and the top surface 600 of the base 110 both should be recessed within the burr hole so that the top surfaces 164, 600 are at approximately the same level as the top 215 of the burr hole 200, the proximally-extending portion 210 of the lead 203 should not be forced to bend in any sharp angles from the point at which the lead segment 206 is secured in the burr hole cover 100.

The surgeon may connect a proximal end (not shown) of the lead 203 to another implanted or external device or otherwise arrange the lead so that it might be proximally connected in a subsequent procedure. Optionally, the user can further dress a portion of the lead extending proximally of the burr hole cover 100 on the patient's skull by, for example, tacking the lead down to the cranial bone with a staple or suture or the like. This may be accomplished before or after the burr hole cover 100 is completely installed (i.e., before or after the cap 160 has been fitted into the base 110 or locked into the base 110.). More often than not, however, this further lead dressing will occur after the surgeon has finished installing the burr hole cover. The surgeon may coil up the remaining proximal portion of the lead and replace the patient's scalp over the surgical field, with the intention of connecting a proximal end of the lead (not shown) to external monitoring equipment or a test stimulator or to another implanted medical device, such as an implanted neurostimulator.

In the event it becomes necessary or desirable to remove a burr hole cover 100 or a lead segment 206 from a burr hole cover, the lead segment 206 can be released by rotating the cap 160 counterclockwise (or to the left) relative to the base 110, for example, by placing forceps in the cap recessions 163.

Thus, embodiments provide for securing a lead to a burr hole with a two-component burr hole cover have been described which avoid sharp transitions and edges on either side of the burr hole and which provide virtually no profile extending above the top of the burr hole except perhaps for bone-attaching pads that are vertically offset from a top surface of the base of the burr hole cover. A relatively small portion of the lead or other medical device is fixated in the burr hole cover as compared to the overall length of the lead or other medical device. Thus, the stresses on the lead or medical device are controlled at the point of fixation.

Various example embodiments are thus described. All statements herein reciting principles, aspects, and embodiments as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope, therefore, is not intended to be limited to the embodiments shown and described herein but rather is defined by the appended claims.

What is claimed is:

1. A burr hole cover for securing a portion of a medical device within a burr hole formed in a patient's cranium, the burr hole cover comprising:
    a base provided with a cap-receiving aperture, a plurality of base channels, and at least one slot having a locking pocket provided in the at least one slot of the base; and
    a cap provided with a corresponding cut-out for each channel of the plurality of base channels provided in the base, and a locking protrusion dimensioned to fit within the at least one slot of the base,
    wherein the cap is configured to be placed in the cap-receiving aperture and to transition, through rotational movement of the cap relative to the base, between 1) an unlocked position during which the locking protrusion is vertically aligned with an axis of the at least one slot and the locking protrusion is disengaged from the locking pocket of the at least one slot of the base, and 2) a locked position during which the locking protrusion is offset from the axis of the at least one slot and the locking protrusion is engaged with the locking pocket of the at least one slot of the base.

2. The burr hole cover of claim 1 wherein the cap further comprises at least one recession configured to receive a surgical tool to assist in manipulating the cap relative to the base.

3. The burr hole cover of claim 1 wherein the base is characterized by a base circumference and further comprises at least one pad vertically offset from and extending away from the base circumference.

4. The burr hole cover of claim 3 wherein the at least one pad has a bottom surface aligned with a top surface of the base such that when the base is positioned in the burr hole, the top surface of the base is situated in a plane that is at or below a surface of the cranium at the burr hole.

5. The burr hole cover of claim 1 wherein the cap is provided with a plurality of guides in a bottom surface of the cap, each guide corresponding to one of the channels in the plurality of base channels.

6. The burr hole cover of claim 5 wherein each of the plurality of guides is further configured to contact a length of the medical device during or after the burr hole cover is installed in the patient.

7. The burr hole cover of claim 1, wherein each channel and the corresponding cut-out are horizontally aligned with each other when the cap is in the unlocked position.

8. The burr hole cover of claim 7, wherein each channel and the corresponding cut-out form an aperture when the channel and the corresponding cut-out are horizontally aligned, the aperture configured to receive the medical device.

9. The burr hole cover of claim 1, wherein each channel and the corresponding cut-out are horizontally offset from each other when the cap is in the locked position.

10. The burr hole cover of claim 9, wherein a radius of the corresponding cut-out is configured to engage the medical device when the channel and the corresponding cut-out are horizontally offset.

* * * * *